(12) United States Patent
Haskell-Luevano et al.

(10) Patent No.: US 7,034,004 B2
(45) Date of Patent: Apr. 25, 2006

(54) PEPTIDES AND METHODS FOR THE CONTROL OF OBESITY

(75) Inventors: Carrie Haskell-Luevano, Archer, FL (US); Jerry Ryan Holder, Simi Valley, CA (US)

(73) Assignee: University of Florida, Gainesville, FL (US)

( * ) Notice: Subject to any disclaimer, the term of this patent is extended or adjusted under 35 U.S.C. 154(b) by 538 days.

(21) Appl. No.: 10/139,624

(22) Filed: May 7, 2002

(65) Prior Publication Data

US 2003/0212002 A1    Nov. 13, 2003

(51) Int. Cl.
*A61K 38/07* (2006.01)
*C07K 5/107* (2006.01)
*C07K 5/117* (2006.01)

(52) U.S. Cl. .................................... 514/18; 530/330
(58) Field of Classification Search ................. 514/18; 530/330
See application file for complete search history.

(56) References Cited

U.S. PATENT DOCUMENTS

| | | | | |
|---|---|---|---|---|
| 5,420,109 A | 5/1995 | Suto et al. | ...... | 514/8 |
| 5,726,156 A | 3/1998 | Girten et al. | ...... | 514/16 |
| 5,741,774 A | 4/1998 | Girten et al. | ...... | 514/8 |
| 5,760,001 A | 6/1998 | Girten et al. | ...... | 514/16 |
| 5,786,332 A | 7/1998 | Girten et al. | ...... | 514/16 |
| 5,888,969 A | 3/1999 | Girten et al. | ...... | 514/8 |
| 5,908,609 A | 6/1999 | Lee et al. | ...... | 424/9.2 |
| 6,245,738 B1 | 6/2001 | Suto et al. | ...... | 514/8 |
| 6,284,735 B1 | 9/2001 | Girten et al. | ...... | 514/16 |
| 6,613,874 B1 * | 9/2003 | Mazur et al. | ...... | 530/317 |
| 2001/0056179 A1 * | 12/2001 | Chen et al. | ...... | 530/330 |

FOREIGN PATENT DOCUMENTS

WO    WO 97/47316    12/1997

OTHER PUBLICATIONS

Jerry Ryan Holder et al., "Structure-Activity Relationships of the Melanocortin Tetrapeptide Ac-His-Dphe-Arg-Trp-NH₂ at Mouse Melanocortin Receptors. I. Modifications at the His Position", J. Med. Chem. 2002, 45, pp 2801-2810.

Jerry Ryan Holder et al., "Structure-Activity Relationships of the Melanocortin Tetrapeptide Ac-His-Dphe-Arg-Trp-NH₂ at Mouse Melanocortin Receptors:Part .Modifications at the Phe Position", J. Med. Chem. 2002, 45, pp 3073-3081.

I. Lee et al., "Change in Body Weight and Longevity", Oct. 21, 1992, JAMA, vol. 268, No. 15, pp 2045-2049.

J. McGinnis et al., "Actual Causes of Death in the United States", Nov. 10, 1993, MA., vol. 270, No. 18, pp 2207-2212.

G. Colditz G., Economic Costs of Obesity [1-3], 1992 AM J. Clin Nutr. 55, pp 503S-507S.

"Methods for Voluntary Weight Loss and Control", NIH Technology Assessment Conference Panel, 1993, Ann Intern Med. vol. 119, No. 7, pp 764-770.

"Long-Term Pharmacotherapy in the Management of Obesity", National Task Force on Obesity, 1996, JAMA, vol. 276, No. 23, pp 1907-1915.

F. Greenway, "Surgery for Obesity", Endo Metab Clin N Amer., vol. 25, (4), Dec. 1996, pp 1005-1027.

S. Long et al., "Weight Loss in Severely Obese Subjects Prevents the Progression of Impaired Glucose Tolerance to Type II Diabetes", May 1994, Diabetes Care, vol. 17, No. 5, pp 372-375.

"Gastrointestnal Surgery for Severe Obesity", NIH Conference, Dec. 1991, Ann Intern Med., vol. 115, No. 12, pp 956-961.

C. Ezzell, "Fat Times for Obesity Research: Tons of New Information, But How Does it All Fit Together", J. NIH Res. 7, pp 39-43(Oct. 1995).

(Continued)

*Primary Examiner*—Jeffrey Edwin Russel
(74) *Attorney, Agent, or Firm*—Saliwanchik, Lloyd & Saliwanchik

(57) ABSTRACT

The subject invention provides novel peptides for use in treating mammals to control appetite and obesity. Disclosed is a peptide derivative having the formula:

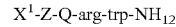

$X^1$-Z-Q-arg-trp-$NH_{12}$ wherein: $X^1$ is an acyl group, Z is amino-2-naphthylcarboxylic acid or histidine, Q is (D)phenylalanine or p-iodo-(D)phenylalanine, or a pharmacologically acceptable salt, complex or derivative thereof, the peptide derivative having melanocortin-4 receptor agonist activity.

12 Claims, 4 Drawing Sheets

OTHER PUBLICATIONS

Trish Gura, "Obesity Sheds Its Secrets", Science, vol. 275, pp 751-753 (Feb. 7, 1997).

Jeffrey S. Flier, "Leptin Expression and Action: New Experimental Paradigms", Proc. Natl. Acad. Sci. USA 94 (1997), pp 4242-4245 (Apr. 1997).

W. Chen et al., "Exocrine Gland Dysfunction in MC5-R-Deficient Mice: Evidence for Coordinated Regulation of Exocrine Gland Function by Melanocortin Peptides", Cell, Dec. 1997, vol. 91, pp 789-798.

W. Fan et al., "Role of Melanocortinergic Neurons in Feeding and the Agouti Obesity Syndrome", Nature, Jan. 1997, vol. 385, pp 165-168.

D. Huszar et al., "Targeted Disruption of the Melanocortin-4 Receptor Results in Obesity in Mice", Cell, Jan. 1997, vol. 88, pp 131-141.

A.A. Butler et al., "A Unique Metabolic Syndrome Causes Obesity in the Melanocortin-3 Receptor-Deficient Mouse", Endocrinology, 2000, vol. 141, No. 9, pp 3518-3521.

A.S. Chen et al., "Inactivation of the Mouse Melanocortin-3 Receptor Results in Increased Fat Mass and Reduced Lean Body Mass.", Nat Genet, Sep. 2000, vol. 26, pp 97-102.

D. Lu et al., "Agouti Protein is an Antagonist of the Melanocyte-Stimulating-Hormone Receptor", Nature, Oct. 1994, vol. 371, pp 799-802.

J.R. Shutter et al., "Hypothalamic Expression of ART, a Novel Gene Related to Agouti, is Up-Regulated in Obese and Diabetic Mutant Mice", Genes & Development, 1997, vol. 11, pp 593-602.

M.M. Ollman et al., "Antagonism of Central Melanocortin Receptors in Vitro and in Vivo by Agouti-Related Protein", Science, Oct. 1997, vol. 278, pp 135-138.

C. Haskell-Luevano et al., "Characterization of Melanocortin NDP-MSH Agonist Peptide Fragments at the Mouse Central and Peripheral Melanocortin Receptors", J. Med. Chem., 2001, vol. 44, pp 2247-2252.

Y. Yang et al., "Molecular Determinants of Ligand Binding to the Human Melanocortin-4 Receptor", Biochemistry 2000, vol. 39, pp 14900-14911.

P. Grieco et al., "New Dimensions in the Design of Potent and Receptor Selective Melanotropin Analogues". In *Peptides for the New Millenium, Proceedings of the 16th American Peptide Symposium*, pp 541-542, not dated.

P. Grieco et al., Design and Synthesis of Highly Potent and Selective Melanotropin Analogues of SHU9119 Modified at Position 6, Biochemical and Biophysical Research Communications, vol. 292, No. 4, pp 1075-1080 (2002).

W. Danho et al., Highly Selective Cyclic Peptides for Human Melanocortin-4 Receptor (MC-4 R): Design, Synthesis, Bioactive Conformation, and Pharmacological Evaluation as an Anti-obesity Agent. In *Proceedings of the 2nd International /17th American Peptide Symposium*, pp 701-703 (2001).

M.J. Kavaranq et al., The Development of a Novel Highly Selective and Potent Agonist for Human Melanocortin 4 Receptor In *Proceedings of the 2nd International/17th American Peptide* Symposium, pp 708-709 (2001).

E. Kaiser et al., "Color Test for Detection of Free Terminal Amino Groups in the Solid-Phase Synthesis of Peptides", Anal. Biochem., 1970, vol. 34, pp 595-598.

C. Haskell-Luevano et al., "Structure Activity Studies of the Melanocortin-4 Receptor by In Vitro Mutagenesis: Identification of Agouti-Related Protein (AGRP), Melanocortin Agonist and Synthetic Peptide Antagonist Interaction Determinants", Biochemistry 2001, vol. 40, No. 20, pp 6164-6179.

H. Schild, $pA_2$, A New Scale for the Measurement of Drug Antagonism., Brit. J. Pharmacol. 1947, vol. 2, pp 189-206.

L. Roselli-Rehfuss et al., "Identification of a Receptor for γMelanotropin and Other Proopiomelanocortin Peptides in the Hypothalamus and Limbic System", Proc. Natl. Acad. Sci. USA, Oct. 1993, vol. 90, pp 8856-8860.

I. Gantz et al., "T. Molecular Cloning of a Novel Melancortin Receptor", J. Biol. Chem., Apr. 1993, vol. 268, No. 11, pp 8246-8250.

I. Gantz et al., "Molecular Cloning, Expression, and Gene Localization of a Fourth Melanocortin Receptor", J. Biol. Chem., Jul. 1993, vol. 268, No. 20, pp 15174-15179.

K.G. Mountjoy et al., "Localization of the Melanocortin-4 Receptor (MC4-R) in Neuroendocrine and Automated Control Circuits in the Brain", Mol. Endo. 1994, 8, pp 1298-1308.

F. Al-Obeidi et al., "Design of a New Class of Superpotent Cyclic α-Melanotropins Based on Quenched Dynamic Simulations", J. Am. Chem. Soc. 1989, vol. 111, No. 9, pp 3413-3416.

F. Al-Obeidi et al. Potent and Prolonged Acting Cyclic Lactam Analogues of α-Melanotropin: Design Based on Molecular Dynamics., J. Med. Chem. 1989, vol. 32, No. 12, pp 2555-2561.

V.J. Hruby et al., "Cyclic Lactam α-Melanotropin Analogues of Ac-Nle$^4$-c(Asp$^5$,Dphe$^7$, Lys$_{10}$)-α-MSH(4-10)-NH$_2$ with Bulky Aromatic Amino Acids at Position 7 Show High Antagonist Potency and Selectivity at Specific Melanocortin Receptors", J. Med Chem. 1995, vol. 38, No. 18, pp. 3454-3461.

S.C. Benoit et al., "A Novel Selective melanocortin-4 Receptor Agonist Reduces Food Intake in Rats and Mice Without Producing Aversive Consequences", J. Neurosci May 2000, 20(9), pp 3442-3448.

M.A. Bednarek et al., Analogs of MTII, Lactan Derivatives of α-Melanotropin, Modified at the N-Terminus, and their Selectivity at Human Melanocortin Receptors 3, 4, and 5, Biochem. Biophys. Res. Commun. 1999, vol. 261, No. 1, pp 209-213.

M.A. Bednarek et al., "Potent and Selective Peptide Agonists of α-Melanotropin Action at Human Melanocortin Receptor 4: Their Synthesis and Biological Evaluation in Vitro", Biochem. Biophys. Res. Commun., 2001, vol. 286, No. 3, 641-645.

Bednarek, M.A. et al. "Analogs of Lactam Derivatives of α-Melanotropin with Basic and Acidic Residues" Biochemical and Biophysical Research Communications, 2000, pp. 23-28, vol. 272.

Haskell-Luevano, C. et al. "Truncation Studies of α-Melanotropin Peptides Identify Tripeptide Analogues Exhibiting Prolonged Agonist Bioactivity" Peptides, 1996, pp. 995-1002, vol. 17, No. 6.

Haskell-Luevano, C. "Discovery of Prototype Peptidomimetic Agonists at the Human Melanocortin Receptors MC1R and MC4R" J. Med. Chem., 1997, pp. 2133-2139, vol. 40.

* cited by examiner

PEPTIDES AND METHODS FOR THE CONTROL OF OBESITY

The work reported herein was supported by NIH Grant RO1-DK57080. Accordingly, the U.S. Government has certain rights in the invention.

BACKGROUND OF THE INVENTION

1. Field of the Invention

This invention relates generally to certain peptides and to methods and pharmaceutical compositions incorporating such peptides, for treating mammals to control appetite and obesity.

2. Description of the Prior Art

Obesity is a well established risk factor for a number of potentially life-threatening diseases such as atherosclerosis, hypertension, diabetes, stroke, pulmonary embolism, and cancer. Furthermore, it complicates numerous chronic conditions such as respiratory diseases, osteoarthritis, osteoporosis, gall bladder disease, and dyslipidemias. The enormity of this problem is best reflected in the fact that death rates escalate with increasing body weight. More than 50% of all-cause mortality is attributable to obesity-related conditions once the body mass index (BMI) exceeds 30 kg/m.sup.2, as seen in 35 million Americans. (Lee 1992. JAMA. 268:2045–2049). By contributing to greater than 300,000 deaths per year, obesity ranks second only to tobacco smoking as the most common cause of potentially preventable death. (McGinnis 1993 MA.270:2207–2212). Accompanying the devastating medical consequences of this problem is the severe financial burden placed on the health care system in the United States. The estimated economic impact of obesity and its associated illnesses from medical expenses and loss of income are reported to be in excess of $68 billion/year. (Colditz G. 1992. Am J Clin Nutr. 55:503S–507S). This does not include the greater than $30 billion per year spent on weight loss foods, products, and programs. (Wolf 1994. Pharmacoeconomics. 5:34–37).

A major reason for the long-term failure of established approaches is their basis on misconceptions and a poor understanding of the mechanisms of obesity. Conventional wisdom maintained that obesity is a self-inflicted disease of gluttony. Comprehensive treatment programs, therefore, focused on behavior modifications to reduce caloric intake and increase physical activity using a myriad of systems. These methods have limited efficacy and are associated with recidivism rates exceeding 95%. (NIH Technology Assessment Conference Panel. 1993. Ann Intern Med. 119:764–770). Failure of short-term approaches, together with the recent progress made in elucidating the pathophysiology of obesity, have lead to a reappraisal of pharmacotherapy as a potential long-term, adjuvant treatment. (National Task Force on Obesity. 1996. JAMA. 276:1907–1915). The premise is that body weight is a physiologically controlled parameter similar to blood pressure and obesity is a chronic disease similar to hypertension. The goal of long-term (perhaps life long) medical therapy would be to facilitate both weight loss and subsequent weight maintenance in conjunction with a healthy diet and exercise. To assess this approach, the long-term efficacy of currently available drugs must be judged against that of non-pharmacological interventions alone. Currently, no single drug regimen emerges as superior in either promoting or sustaining weight loss. Although promising, the success of this approach is limited by the efficacy of currently available anorexiant drugs. Surgical interventions, such as gastric partitioning procedures, jejunoileal bypass, and vagotomy, have also been developed to treat severe obesity. (Greenway 1996. Endo Metab Clin N Amer. 25:1005–1027). Although these procedures induce similar rates of early weight loss as nonsurgical interventions, they have been shown to maintain a weight loss of up to 33% for more than 10 years. (Long 1994. Diabetes Care. 17:372–375). While still far from optimal, this is a substantial improvement over that achieved with behavioral and medical management alone. The superior long-term outcome with surgical procedures in attributed to the inherent permanence of the intervention which addresses the chronic nature of the disease. Although advantageous in the long run, the acute risk benefit ratio has reserved these invasive procedures for morbidly obese patients according to the NIH consensus conference on obesity surgery (BMI>40 kg/m.sup.2). (NIH Conference. 1991. Ann Intern Med. 115:956–961). Therefore, this is not an alternative for the majority of overweight patients unless and until they become profoundly obese and are suffering the attendant complications.

Existing pharmacotherapeutic approaches to weight loss involve the use of amphetamine-based agents such as amphetamine, diethylpropion, mazindol and fenfluramine which act directly on the CNS to lower food intake by modulating dopaminergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions other drugs such as MAO inhibitors and antihypertensives. There is also a subpopulation of obese patients that is refractory to present anorectic drug treatments. The medical need is high for an effective anorectic agent which overcomes the above disadvantages of existing therapies. Of particular need are agents which act by alternative mechanisms to modulate food intake and/or metabolism.

No one knows all of the mechanisms involved in regulation of weight gain, although it is believed that many genetic as well as environmental factors, including diet and exercise, play major, interrelated roles. A number of publications have reported the discovery of genes that have been "knocked out" or overexpressed in transgenic mice, resulting in affected animals becoming incredibly obese, or vice versa. See, for example, Ezzell, "Fat Times for Obesity Research: Tons of New Information, but How Does It All Fit Together" J. NIH Res. 7, 39–43 (October 1995). Researchers have reported the cloning of at least two distinct genes, Ob which encodes a protein "leptin" believed to cause weight reduction in obese animals, and Db, which is believed to cause weight gain in animals. Other genes which have been reported include the fat, tub, agouti, and melanocortin 4 receptor genes. Recent reviews relating to the insights regarding the mechanisms involved in obesity help to understand these complex pathways. See, for example, Trish Gura, Science 275, 752–753 (Feb. 7, 1997) and Jeffrey S. Flier, Proc. Natl. Acad. Sci. USA 94, 4242–4245 (April 1997). Leptin, discovered in 1994 by Jeffrey Friedman's team at Rockefeller University, NY, is a 16 kD protein produced by the obesity (ob) gene of mice. Homozygotes with defective ob genes are unable to reproduce, stay warm, or grow normally, and become grossly overweight. The receptor for leptin has now been identified and cloned. Defects in the receptor also result in grossly obese animals. The receptor is expressed in the brain primarily in four regions, including the arcuate nucleus. In humans, however, the linkage between obesity and overexpression of leptin does not seem to be closely correlated, and no individuals have been identified that have a mutated Ob receptor or gene. Another molecule which appears to be important in weight control is the appetite-stimulating neurotransmitter referred to as neuropeptide Y or "NPY". NPY levels are elevated in animals with decreased levels of leptin. Genetic studies with knockout NPY and ob/ob animals indicate that NPY plays a role in, but is not a controlling factor, in obesity. Another line of research has implicated a role in obesity for the melanocortin receptor ("MCR"). Two MCRs, MCR3 and MCR4, are produced in the arcuate nucleus of the hypothalamus, a prime target of leptin action as well as of NPY production. Synthetic peptides mimicking melanocortins which bind to MCR-4 suppress feeding. Animals in which the gene encoding MCR-4 has been knocked out show the opposite behavior, exhibiting high weight gain and high NPY expression.

These genetic studies have clarified, but not definitively determined, the factors which are responsible for obesity, nor provided compounds for treatment or prevention of obesity.

It is therefore an object of the present invention to provide novel agents, methods and compositions for regulating obesity and for controlling appetite.

SUMMARY OF THE INVENTION

One embodiment of the invention relates to peptide derivatives having the formula:

$$X^1\text{-Z-Q-arg-trp-NH}_2$$

Wherein: $X^1$ is an acyl group,

Z is amino-2-naphthyl-carboxylic acid or histidine,

Q is (D)phenylalanine or p-iodo-(D)phenylalanine, or a pharmacologically acceptable salt, complex or derivative thereof, wherein the peptide derivative has melanocortin-4 receptor agonist activity.

A further embodiment of the invention concerns a composition for the treatment of obesity and the control of appetite in a mammal comprising an effective amount of a peptide derivative as described above in combination with a carrier therefore.

An additional embodiment of the invention is a method for the treatment of obesity and control of appetite in a mammal comprising administering to a mammal in need thereof an effective amount of a peptide derivative as described above.

Figure 1:
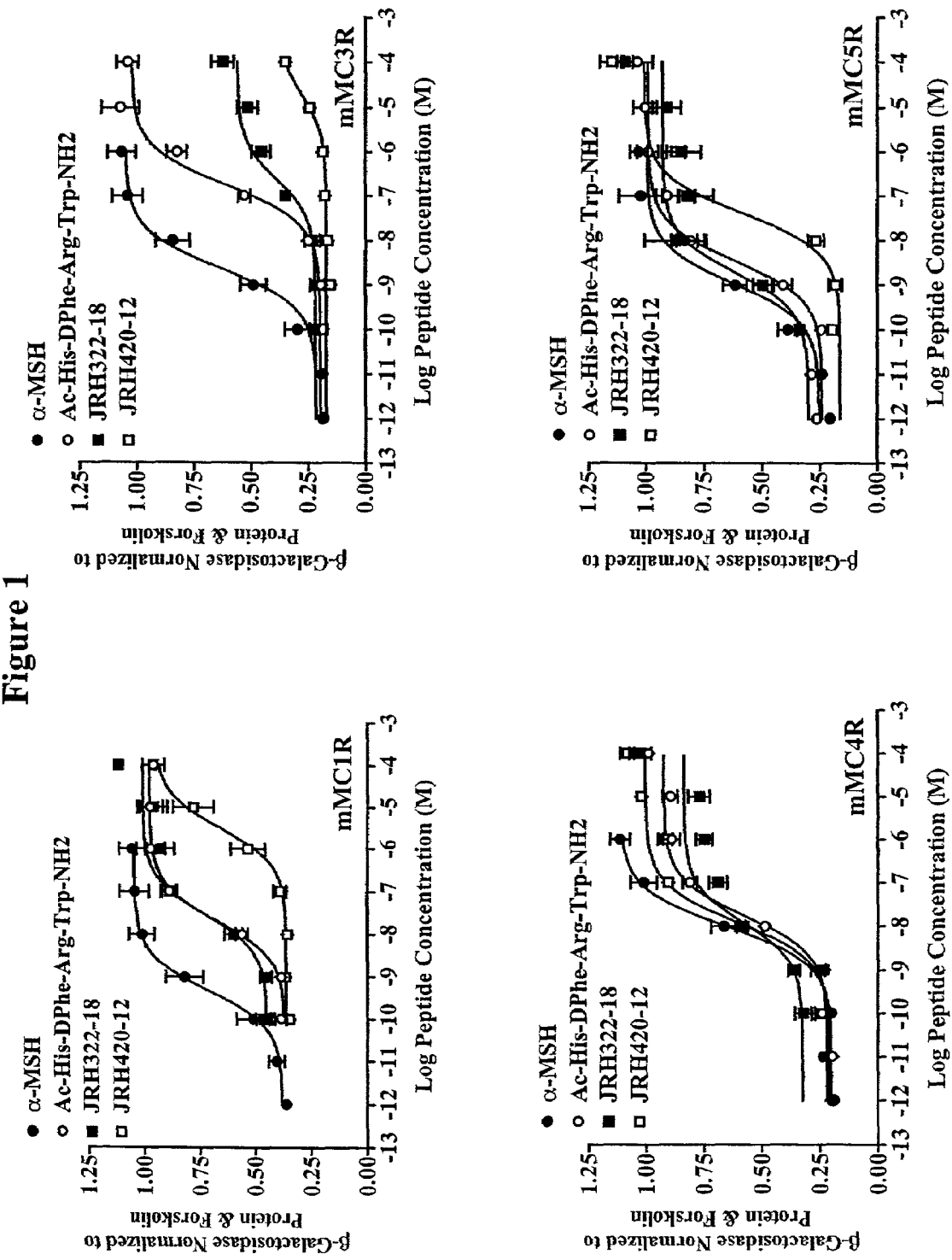
FIG. 1 is an illustration of melanocortin tetrapeptide agonist pharmacology at the mouse melanocortin receptors MC1R, MC3R, MC4R, and MC5R.

The present invention pertains to novel peptides for treating and/or controlling obesity and appetite. The peptides of the invention, as compared to SEQ ID NO:1 (His-Phe-Arg-Trp) and endogenous α-MSH SEQ ID NO:2 (AC-Ser-Tyr-Ser-Met-Glu-His$^6$-Phe-Arg-Trp-Gly-Lys-Pro-Val-NH$_2$), have demonstrated potent melanocortin-4 receptor agonist activity versus melanocortin-3 receptor selectivity.

SEQ ID NO:1 is a sequence contained in all endogenous melanocortin agonists.

SEQ ID NO:2 is the endogenous melanocortin agonist hormone α-MSH.

DETAILED DESCRIPTION OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified.

Evidence for the involvement of MC-Rs in obesity includes: i) the agouti (A$^{vy}$) mouse which ectopically expresses an antagonist of the MC-1R, MC-3R and -4R is obese, indicating that blocking the action of these three MC-Rs can lead to hyperphagia and metabolic disorders; ii) MC-4R knockout mice (Huszar et al., Cell, 88, 131–141, 1997) recapitulate the phenotype of the agouti mouse and these mice are obese; iii) the cyclic heptapeptide MT-II (MC-1R, -3R, -4R, -5R, agonist) injected intracerebroventricularly (ICV) in rodents, reduces food intake in several animal feeding models (NPY, ob/ob, agouti, fasted) while ICV injected SHU-9119 (MC-3R, -4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R and -5R and to attenuate food intake and body weight gain over a 12 week period.

Five MC-Rs have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. MC-5R is expressed in many tissues including white fat, placenta and exocrine glands. A low level of expression is also observed in the brain. MC-5R knock out mice reveal reduced sebaceous gland lipid production (Chen et al., Cell, 1997, 91, 789–798).

Named by number in the order of their discovery, the melanocortin-1 receptor gene has been found thus far to be expressed primarily in the epidermal tissues; melanocortin-3, melanocortin-4, and melanocortin-5 receptor genes have been found thus far to be expressed primarily in the hypothalamus, mid-brain and brainstem (MC3-R, and MC4-R), or in a wide distribution of peripheral tissues (MC5-R).

The melanocortin peptides have been reported to have a wide variety of biological activities, known to be mediated by the MSH and ACTH receptors. However, given the complexity of possible sites of expression of the MC3, MC4 and MC5 receptors, it has not been possible to unambiguously identify any simple correlation between these receptors and the reported biological activities of their ligands.

The MCR-4 receptor is implicated in body weight regulation. For example, inventors Gu et al. describe using melanocortin-4 receptor as a target to treat body weight disorders by modulating the activity of that receptor, WO 97/47316, published Dec. 18, 1997.

One embodiment of the present invention is predicated on the discovery that the above-described tetrapeptide (JRH322-18) unexpectedly and unobviously possesses partial agonist and antagonist pharmacology at the MC3R receptor and also functions as a potent agonist at the MC4R receptor. Thus the peptide derivative possesses unexpected pharmacology at the brain melanocortin receptors involved in feeding behavior and obesity, and also operate as an agonist at the MC4R receptor rendering it a therapeutic agent for decreasing obesity and obesity-related diseases such as hypertension, type II diabetes, stroke, cancer and morbidity.

As noted above, the melanocortin system, consisting of endogenous agonists, antagonists, and centrally located G-protein coupled receptors, has been implicated as physiologically participating in the centrally mediated process of energy homeostasis and obesity. The melanocortin-3 and melanocortin-4 receptors are located in the hypothalamus of the brain and are stimulated by the melanocortin agonists and antagonized by the agouti-related-protein (AGRP). Ligands selective for either one of these central melanocortin receptors are desired as tools to clearly differentiate the physiological roles that the MC3 and MC4 receptors are regulating in the brain. The present invention is predicated on the discovery of two tetrapeptides that are substituted at the His and Phe position with amino-2-napthyl carboxylic acid (Anc) and para-iodo-D-phenylalanine (pIDPhe), respectively. The peptide, Ac-Anc-DPhe-Arg-TrpNH$_2$ (JRH420-12) possesses a potent mMC4R agonist EC$_{50}$ value of 21 nM and is a weak mMC3R antagonist (pA$_2$=5.60 Ki=2.5 nM). The peptide, Ac-His-(pI)DPhe-Arg-Trp-NH$_2$ (JRH322-18 ) is a potent mMC4R agonist with an EC$_{50}$ value of 25 nM and a potent mMC3R antagonist (pA$_2$=7.25 Ki=56 nM). Both JRH 420-12 and JRH 322-18 also possessed nm potency at the human MC4R.

Again, The energy homeostasis and obesity. [Fan, W. et al, Role of Melanocortinergic Neurons in Feeding and the agouti Obesity Syndrome. Nature 1997, 385, 165–168; Huszar, D. et al, Targeted central melanocortin-3 (MC3R) and melanocortin-4 (MC4R) receptors are involved in the regulation of Disruption of the Melanocortin-4 Receptor Results in Obesity in Mice, Cell 1997, 88, 13 1–141; Butler, A. A. et al, A Unique Metabolic Syndrome Causes Obesity in the Melanocortin-3 Receptor-deficient Mouse. Endocrinology 2000, 141, 3518–21; Chen, A. S. et al, Inactivation of the Mouse Melanocortin-3 Receptor Results in Increased Fat Mass and Reduced Lean Body Mass. Nat Genet 2000, 26, 97–102]. These receptors belong to the melanocortin pathway that consists of five melanocortin receptors cloned to date (MC 1–5R), the endogenous agonists derived from the pro-opiomelanocortin (POMC) gene, α-, β-, γ-melanocyte stimulating hormones (MSH) and adrenocorticotropin (ACTH), the only two naturally occurring antagonists of G-protein coupled receptors (GPCRs) identified to date, agouti and agouti-related protein (AGRP), and stimulate the cAMP signal transduction pathway. [The Melanocortin Receptors; Cone, R. D., Ed.; The Humana Press Inc.,: New Jersey, 2000; Lu, D. et al, Agouti Protein is an Antagonist of the Melanocyte-Stimulating-Hormone Receptor. Nature 1994, 371, 799–802; Shutter, J. R. et al, Hypothalamic Expression of ART, a Novel Gene Related to Agouti, is Up-Regulated in Obese and Diabetic Mutant Mice. Genes & Development 1997, 11, 593–602; Ollmann, M. M.; et al, Antagonism of Central Melanocortin Receptors in Vitro and in Vivo by Agouti-Related Protein. Science 1997, 278, 135–138.] Due to the observations that both the MC3R and MC4R are located in the hypothalamus of the brain and are involved in the complex neuroendocrine process of energy homeostasis, ligands selective for either of these melanocortin receptor isoforms are highly sought after as tools to clearly distinguish the independent physiological roles of the MC4R versus the MC3R.

The endogenous melanocortin agonists all contain a central His-Phe-Arg-Trp (SEQ ID NO:1) sequence that has been attributed to the ligand selectivity and stimulation of the melanocortin receptors. It has been reported that the Ac-His-DPhe-Arg-Trp-NH$_2$ tetrapeptide possesses 8 to 10 nM agonist activity at both the mouse [Haskell-Luevano, C. et al, Characterization of Melanocortin NDP-MSH Agonist Peptide Fragments at the Mouse Central and Peripheral Melanocortin Receptors. J. Med. Chem. 2001, 44, 2247–2252] and human [Yang, Y. et al, Molecular Determinants of Ligand Binding to the Human Melanocortin-4 Receptor. Biochemistry 2000, 39, 14900–14911] MC4 receptors. Based upon these data, and information that modification at the His position of larger cyclic peptides, [Grieco, P., et al, New Dimensions in the Design of Potent and Receptor Selective Melanotropin Analogues. In *Peptides for the New Millenium, Proccedings of the 16th American Peptide Symposium*; G. B. Fields, Tam, J. P., and Barany, G., Eds.; Kiuwer: The Netherlands, 2000; pp 541–542; Grieco, P. et al, Synthesis and Conformational Studies of Cyclic Peptides with Antagonist Activity at Melanocortin 3 and 4 Receptors. In *Proceedings of the 26th European Peptide Symposium*; J. a. F. Martinez, J-A., Eds.; EDK: Paris, 2001; pp 643–644; Danho, W. et al, Highly Selective Cyclic Peptides for Human Melanocortin-4 Receptor (MC-4 R): Design, Synthesis, Bioactive Conformation, and Pharmacological Evaluation as an Anti-obesity Agent. In *Proceedings of the 2nd International/17th American Peptide Symposium*; G. Barany, Fields, G. B., Lebel M., Houghten, R., Eds.; Kiuwer Academic Publishers: The Netherlands, in press; Kavarana, M. J. et al, The Design and Evaluation of a Novel Selective and Potent Agonist of the Human Melanocortin Receptor 4. In *Proccedings of the 2nd International/17th American Peptide Symposium*; G. Barany, Fields, G. B., Lebel M., Houghten, R., Eds.; Kluwer Academic Publishers: The Netherlands, in press.] resulted in potent and MC4R selective peptides. Herein, tetrapeptides possessing the amino-2-napthyl carboxylic acid (Anc) at the six position and para-iodo-D-phenylalanine (pIDPhe) at the seven position (α-MSH numbering) were synthesized and pharmacologically evaluated for receptor selectivity, antagonist, and agonist activity at the mouse melanocortin MC1, MC3, MC4, and MC5 receptors.

EXAMPLES

Peptide synthesis was performed using standard Fmoc methodology on an automated synthesizer (Advanced ChemTech 440M05, Louisville, Ky.). The amino acids Fmoc-Anc, Fmoc-(pI)DPhe, Fmoc-His(Trt), Fmoc-Arg (Pbf), Fmoc-DPhe, Fmoc-Trp(Boc) are all commercially available. The coupling reagents 2-(1-H-Benzotriazol-1-yl)-1,1,3,3-tetramethyluronium hexafluorophosphate (HBTU) and 1-Hydroxybenzotriazole (HOBt) are all commercially available. All reagents and chemicals were ACS grade or better and were used without further purification.

The peptides were assembled on rink-amide-MBHA resin (0.44 meq/g substitution) [commercially available]. The synthesis was performed using a 40 well teflon reaction block with a course teflon frit. Approximately 100 mg resin (0.044 mmole) was added to each reaction block well. The resin was allowed to swell for 2 hrs in DMF and deprotected using 25% piperidine in DMF for 5 mm followed by a 20 mm 25% piperidine incubation at 450 rpms. A positive Kaiser [Kaiser, E. et al, Color Test for Detection of Free Terminal Amino Groups in the Solid-Phase Synthesis of Peptides. Anal. Biochem. 1970, 34, 595–598] test resulted, indicating free amine groups on the resin. The growing peptide chain was added to the amide-resin using the general amino acid cycle as follows: 500 μL DMF is added to each reaction well to "wet the frit", 3-fold excess amino acid starting from the C-terminus is added (275 μL of 0.5M amino acid solution containing 0.5M HOBt in DMF) followed by the addition of 275 μL 0.5M DIC in DMF and the reaction well volume is brought up to 3 mL using DMF. The coupling reaction is mixed for 1 hr at 450 rpms, followed by emptying of the reaction block by positive nitrogen gas pressure. A second coupling reaction is performed by the addition of 500 μL DMF to each reaction vessel, followed by the addition of 275 μL of the respective amino acid (3-fold excess), 275 μL 0.5M HBTU, and 225 μL 1M DIEA. The reaction well volume is brought up to 3 mL with DMF and mixed at 450 rpm for 1 hr. After the second coupling cycle, the reaction block is emptied and the Nα-Fmoc-protected peptide-resin is washed with DMF (4.5 mL, 4 times). Nα-Fmoc deprotection is performed by the addition of 4 mL 25% piperidine in DMF and mixed for 5 min at 450 rpms followed by a 20 min deprotection at 450 rpms. The reaction well is washed with DMF (4.5 mL, 4 times) and the next coupling cycle is performed as described above. Following Nα-Fmoc deprotection of the final amino acid, acetylation of the Nα-amine was performed by addition of 2 mL acetic anhydride, 1 mL pyridine and 1 mL DMF to the reaction block wells and mixed for 30 min at 450 rpms. The acetylated peptide-resin was washed with DCM (4 mL, 5 times) and dried thoroughly prior to cleavage from the resin. Deprotection of the amino acid side chains and cleavage of the acetylated-peptide from the resin was performed by incubating the peptide-resin with 3 mL cleavage cocktail (95% TFA, 2.5% water, 2.5% Tis) for 3 hrs at 450 rpms. The cleavage product was emptied from the reaction block into a cleavage block containing 7 mL collection vials under positive nitrogen gas pressure. The resin was washed with 1.5 mL cleavage cocktail for 5 min at 450 rpms and added to the previous cleavage solution. The peptides were transferred to pre-weighed 50 mL conical tubes and precipitated with cold (4° C.) anhydrous ethyl ether (up to 50 mL). The flocculent peptide was pelleted by centrifugation (Sorval Super T21 high speed centrifuge using the swinging bucket rotor) at 4000 rpm for 5 min, the ether was decanted off, and the peptide was washed one time with cold anhydrous ethyl ether and again pelleted. The crude peptide was dried in vacuo for 48 hrs. The crude peptide yields ranged from 60% to 90% of theoretical. A 15 to 30 mg sample of crude peptide was purified by RP-HPLC using a Shimadzu chromatography system with a photodiode array detector and a semi-preparative RP-HPLC $C_{18}$ bonded silica column (Vydac 218TP1010, 1.0×25 cm) and lyophilized. The purified peptides were at least >95% pure as determined by analytical RP-HPLC and had the correct molecular mass [Table 1].

TABLE 1

Analytical data for the peptides synthesized in this study.

| Peptide | Structure | HPLC k' (System 1) | HPLC k' (System 2) | Purity | Mass Spectral Analysis (M + 1) |
|---|---|---|---|---|---|
| JRH279-31 | Ac-His-DPhe-Arg-Trp-NH$_2$ | 3.9 | 6.9 | >98 | 686.3 |
| JRH420-12 | Ac-Anc-DPhe-Arg-Trp-NH$_2$ | 7.3 | 11.1 | >99 | 717.7 |
| JRH322-18 | Ac-His-(pI)DPhe-Arg-Trp-NH$_2$ | 5.0 | 8.3 | >98 | 812.0 |

HPLC k' = [(peptide retention time - solvent retention time)/solvent retention time] in solvent system 1 (10% acetonitrile in 0.1% trifluoroacetic acid/water and a gradient to 90% acetonitrile over 40 min) or solvent system 2 (1(10% methanol in 0.1% trifluroacetic acid/water and a gradient to 90% methanol over 40 min). An analytical Vydac C18 column (Vydac 218TP104) was used with a flow rate of 1.5 mL/min. The percentage peptide purity is determined by HPLC at a wavelength of 214λ.

For cell culture and transfection, briefly, HEK-293 cells were maintained in Dulbecco's modified Eagle's medium (DMEM) with 10% fetal calf serum and seeded 1 day prior to transfection at 1 to 2×10$^6$ cell/100-mm dish. Melanocortin receptor DNA in the pCDNA$_3$ expression vector (20 μg) were transfected using the calcium phosphate method. Stable receptor populations were generated using G418 selection (1 mg/mL) for subsequent bioassay analysis.

In the functional bioassay studies, HEK-293 cells stably expressing the melanocortin receptors were transfected with 4 μg CRE/β-galactosidase reporter gene as previously described in the literature. Briefly, 5,000 to 15,000 post transfection cells were plated into 96 well Primera plates (Falcon) and incubated overnight. Forty-eight hours post-transfection the cells were stimulated with 100 μL peptide ($10^{-4}$–$10^{-12}$ M) or forskolin ($10^{-4}$ M) control in assay medium (DMEM containing 0.1 mg/mL BSA and 0.1 mM isobutylmethylxanthine) for 6 hrs. The assay media was aspirated and 50 µL of lysis buffer (250 mM Tris-HCl pH=8.0 and 0.1% Triton X-100) was added. The plates were stored at 80° C. overnight. The plates containing the cell lysates were thawed the following day. Aliquots of 10 µL were taken from each well and transferred to another 96-well plate for relative protein determination. To the cell lysate plates, 40 µL phosphate-buffered saline with 0.5% BSA was added to each well. Subsequently, 150 µL substrate buffer (60 mM sodium phosphate, 1 mM $MgCl_2$, 10 mM KCl, 5 mM β-mercaptoethanol, 200 mg ONPG) was added to each well and the plates were incubated at 37°. The sample absorbance, $OD_{405}$, was measured using a 96 well plate reader (Molecular Devices). The relative protein was determined by adding 200 µL 1:5 dilution Bio Rad G250 protein dye:water to the 10 µL cell lysate sample taken previously, and the $OD_{595}$ was measured on a 96 well plate reader (Molecular Devices). Data points were normalized both to the relative protein content and non-receptor dependent forskolin stimulation. The antagonistic properties of these compounds were evaluated by the ability of these ligands to competitively displace the MTII agonist (Bachem) in a dose-dependent manner, at up to 10 µM concentrations [Haskell-Luevano, C. et al, Structure Activity Studies of the Melanocortin-4 Receptor by In Vitro Mutagenesis: Identification of Agouti-Related Protein (AGRP), Melanocortin Agonist and Synthetic Peptide Antagonist Interaction Determinants. *Biochemistry* 2001, 40, 6164–6179.]

pared with the endogenous agonist hormone, α-MSH (Ac-Ser-Tyr-Ser-Met-Glu-His[6]-Phe-Arg-Trp-Gly-Lys-Pro-Val-$NH_2$; SEQ ID NO:2). The Ac-Anc-DPhe[7]-Arg[8]-Trp[9]-$NH_2$ (JRH42O-12) (α-MSH numbering), resulted in 14000-, 4-, and 100-fold decreased potencies at the mMC1R, mMC4R, and mMC5R, respectively, compared to α-MSH. The Ac-His[6]-(pI) DPhe[7]-Arg[8]-Trp[9]-$NH_2$ (JRH 322-18) tetrapeptide resulted in 110-, 5- and 4-fold decreased potencies at the MMC1R, MMC4R, and MMC5R, respectively, compared to α-MSH. The JRH 322-18 tetrapeptide resulted in partial agonist and potent MMC3R antagonist. It is completely unexpected that JRH-420-12 only has weak micro molar (10-6 M) activity at the MC3R and potent nM agonist (10-9 M) activity at the MC4R. Thus, it is >4700-fold selective for the MC4R versus the MC3R. Additionally, it is completely unexpected that JRH 322-18 is a potent MMC3R antagonist, but a potent MC4R agonist. The central melanocortin receptors, MC3R [Roselli-Rehfuss, L. et al, Identification of a Receptor for Melanotropin and Other Propiomelanocortin Peptides in the Hypothalamus and Limbic System. *Proc. Natl. Acad. Sci. USA* 1993, 90, 8856–8860; Gantz, I. et al, T. Molecular Cloning of a Novel Melanocortin Receptor. *J. Biol. Chem.* 1993, 268, 8246–8250] and MC4R [Gantz, I. et al, Molecular Cloning, Expression, and Gene Localization of a Fourth Melanocortin Receptor. *J. Biol. Chem.* 1993, 268, 15174–15179; Mountjoy, K. G. et al, Localization of the Melanocortin-4 Receptor (MC4-R) in Neuroendocrine and Autonomic Control Circuits in the Brain. *Mol. Endo.* 1994, 8, 1298–1308] have been demonstrated to be involved in the complex neuroendocrine process of energy homeostasis and metabolism.

TABLE 2

Functional activity of the tetrapeptide agonists at the mouse melanocortin receptors.

| Peptide | Structure | mMC1R $EC_{50}$ (nM) | mMC3R $EC_{50}$ (nM) | mMC4R EC50 (nM) | mMC5R EC50 (nM) |
| --- | --- | --- | --- | --- | --- |
| α-MSH (SEQ ID NO:2) | Ac-Ser-Tyr-Ser-Met-Glu-His-Phe-Arg-Trp-Gly-Lys-Pro-Val-$NH_2$ | 0.55 ± 0.09 | 0.79 ± 0.14 | 5.37 ± 0.62 | 0.44 ± 0.09 |
| NDP-MSH | Ac-Ser-Tyr-Ser-Nle-Glu-His-DPhe-Arg-Trp-Gly-Lys-Pro-Val-$NH_2$ | 0.038 ± 0.012 | 0.098 ± 0.013 | 0.21 ± 0.03 | 0.071 ± 0.012 |
| MTII | Ac-Nle-c[Asp-His-DPhe-Arg-Trp-Lys]-$NH_2$ | 0.020 ± 0.003 | 0.016 ± 0.03 | 0.087 ± 0.008 | 0.16 ± 0.03 |
| JRH279-31 | Ac-His-DPhe-Arg-Trp-$NH_2$ | 20.1 ± 0.57 | 156 ± 9.2 | 17.2 ± 2.78 | 3.96 ± 0.94 |
| JRH420-12 | Ac-Anc-DPhe-Arg-Trp-$NH_2$ | 7,900 ± 4,200 | Slight agonist $pA_2$ = 5.60 | 21.1 ± 5.96 | 45.6 ± 6.90 |
| JRH322-18 | Ac-His-(pI)DPhe-Arg-Trp-$NH_2$ | 60.4 ± 13.4 | Slight agonist $pA_2$ + 7.25 | 25.0 ± 9.78 | 1.60 ± 0.35 |

The $pA_2$ values were generated using the Schild analysis method [Schild, H. 0. $pA_2$, A New Scale for the Measurement of Drug Antagonism. *Brit. J. Pharmacol.* 1947, 2, 189–206. For data analysis, $EC_{50}$ and $pA_2$ values represent the mean of duplicate experiments performed in quadruplet or more independent experiments. $EC_{50}$ and $pA_2$ estimates, and their associated standard errors, were determined by fitting the data to a nonlinear least-squares analysis using the PRISM program (v3.0, GraphPad Inc.). The results are not corrected for peptide content, although all the peptides examined in this study were determined to have approximately equal peptide content as determined by using Beers Law.

Figure 2:
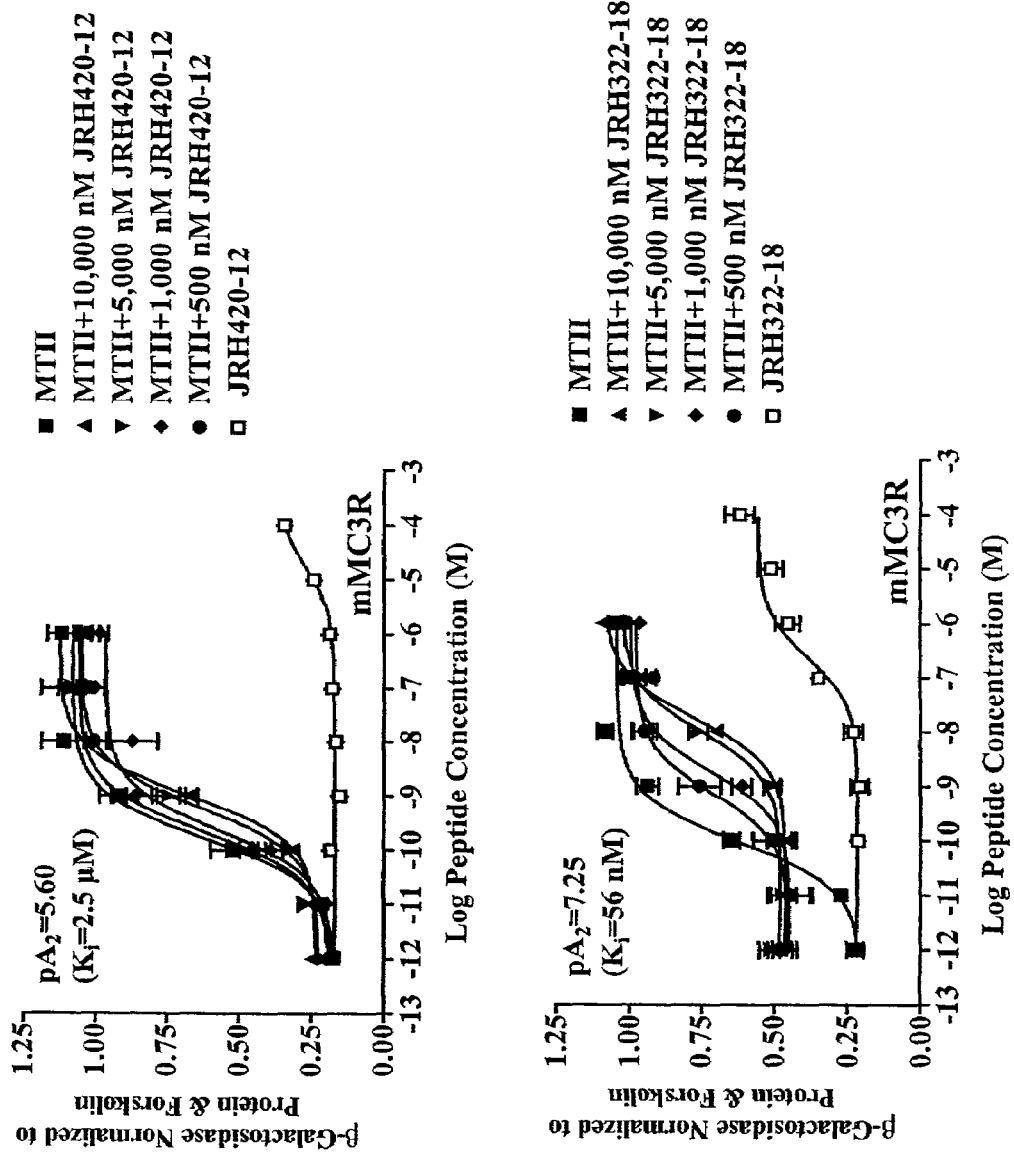
FIG. 2 shows the antagonist pharmacology of the tetrapeptides, SAc-Anc-DPhe-Arg-Trp-NH$_2$ (JRH42O-12) and Ac-His-(pI) Dphe-Arg-Trp-NH$_2$ (JRH322-18), at the mMC3R. The pA$_2$ and Ki values were determined using Schild Analysis where Ki=−Log pA$_2$.
Figure 3:
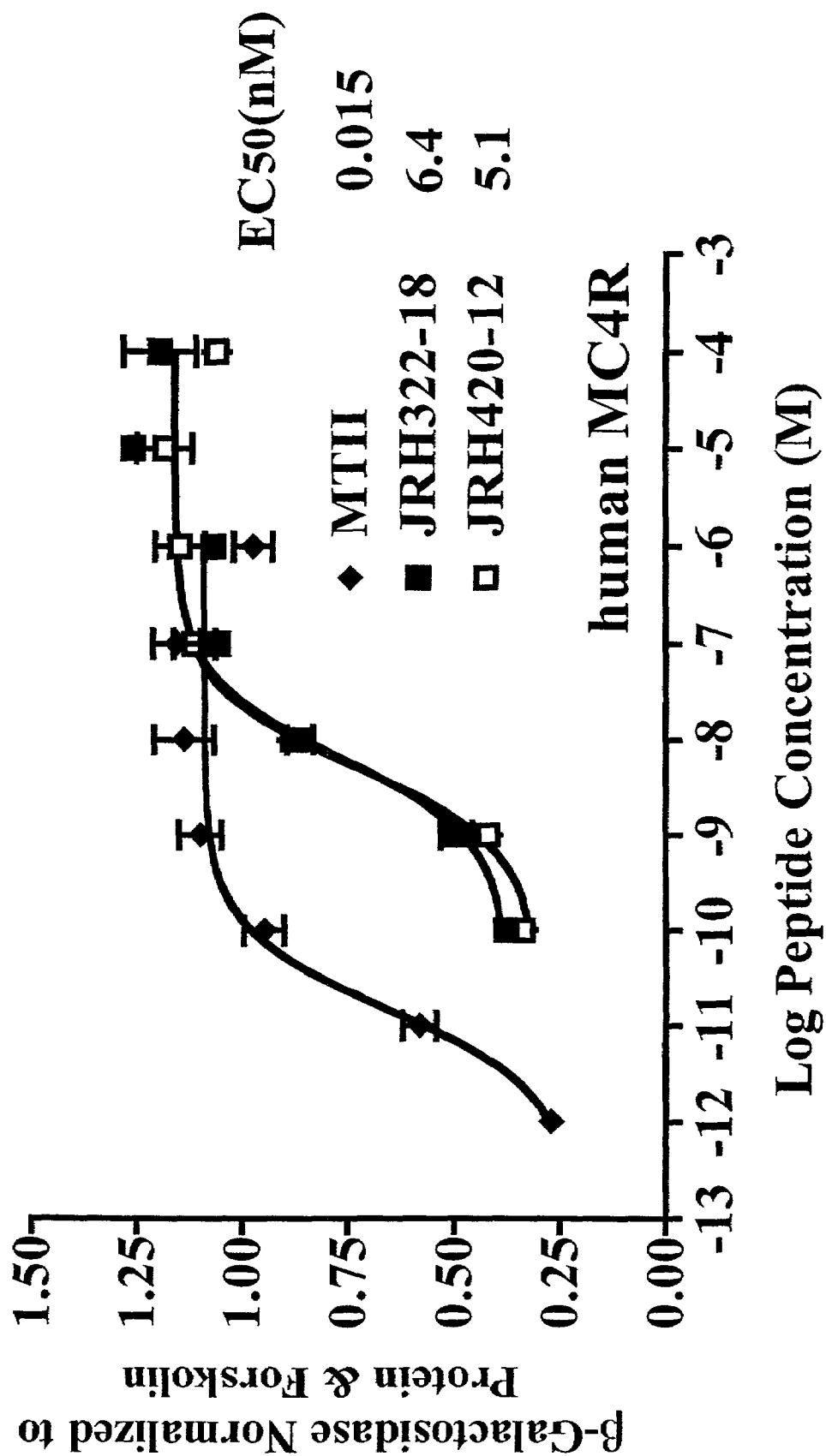
FIG. 3 shows the agonist pharmacology of 3RH 420-12 and JRH 322-18 at the human MC4R.
Figure 4:
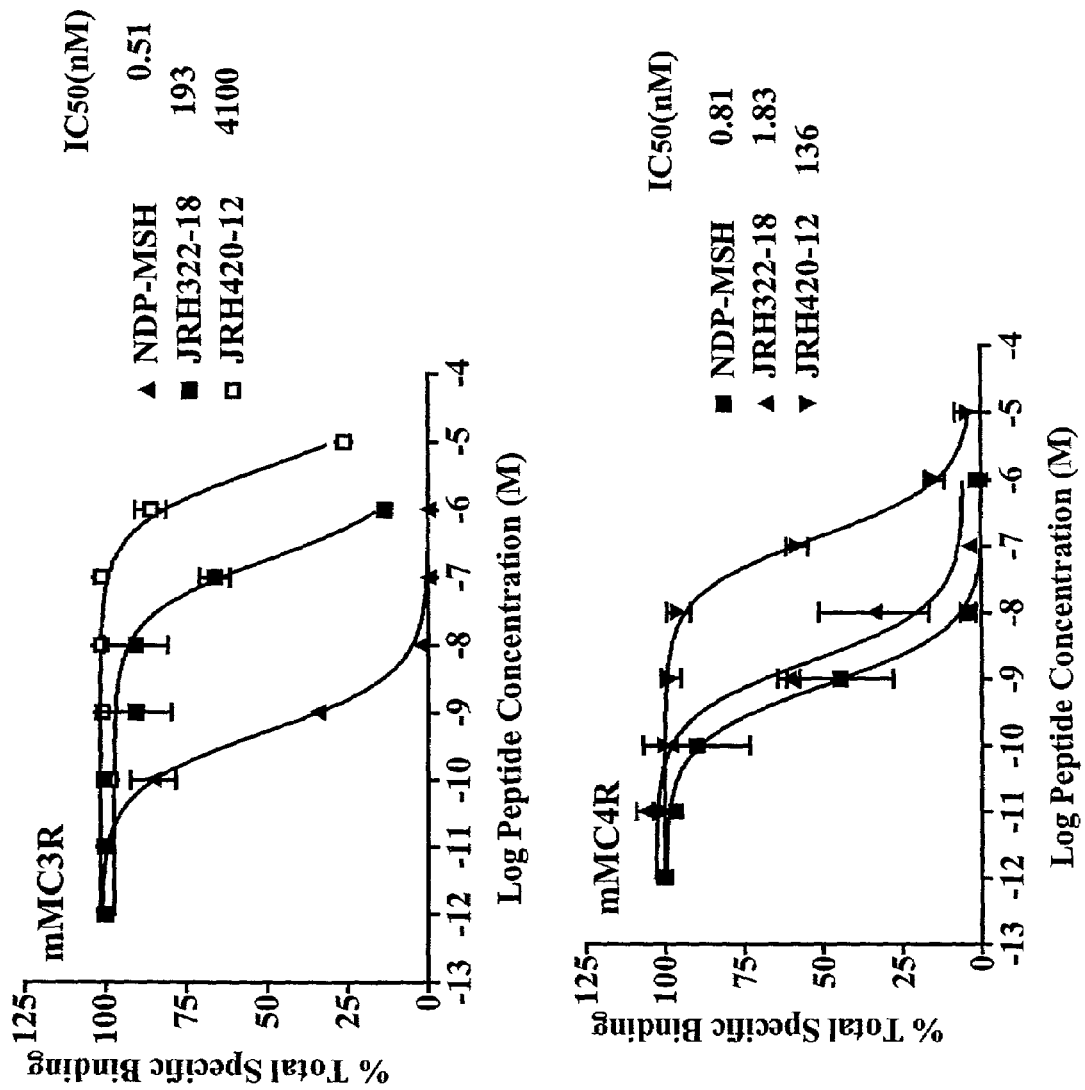
FIG. 4 shows the competitive displacement binding of JRH 420-12 and JRH 322-18 at the MMC3R and MMC4R using the I$^{125}$-NDP-MSH radio label.

Table 2 summarizes the tetrapeptide agonist $EC_{50}$ values and antagonist $pA_2$ values observed at the mouse melanocortin receptors, mMC1R, mMC3R, mMC4R, and mMC5R. FIGS. 1–4 illustrate the pharmacology of the tetrapeptides described herein at these melanocortin receptors, as com- Initial studies implicating the MC4R in feeding behavior were based upon the central administration of the highly potent melanocortin agonist MTII (Ac-Nle-c[Asp-His-DPhe-ArgTrp-Lys]-$NH_2$) [Al-Obeidi, F., et al, Design of a New Class of Superpotent Cyclic α-Melanotropins Based on Quenched Dynamic Stimulations. *J. Am. Chem. Soc.* 1989, 111, 3413–3416; Al-Obeidi, F. et al Potent and Prolonged Acting Cyclic Lactam Analogues of α-Melanotropin: Design Based on Molecular Dynamics. .1. *Med. Chem.* 1989, 32, 2555–2561] into rodents, resulted in decreased food intake, whereas central administration of the MC3R and MC4R antagonist SHU91 19 (Ac-Nle-c[Asp-His-DNal (2')-Arg-Trp-Lys]-$NH_2$) [Hruby, V. J. et al, Cyclic Lactam α-Melanotropin Analogues of Ac-Nle[4]-c(Asp[5], DPhe[7], Lys10)-α-MSH(4–10)-$NH_2$ With Bulky Aromatic Amino Acids at Position 7 Show High Antagonist Potency and Selectivity at Specific Melanocortin Receptors. *J. Med. Chem.* 1995, 38, 3454–3461] resulted in increased food intake. [Fan et al, Nature, v. 385, pp165–168, 1997]. These and other subsequent studies resulted in the hypothesis that the identification of an agonist selective for the MC4R versus the MC3R may result in a potential therapeutic agent for the treatment of obesity by decreasing the desire to eat. This concept has been supported by the identification of a modified peptide agonist, R027-3225 possessing 675-fold agonist MC4 receptor selectivity versus the MC3R and when administered icv to rodents resulted in decreased food intake [Benoit, S. C. et al, A Novel Selective Melanocortin-4 Receptor Agonist Reduces Food Intake in Rats and Mice Without Producing Aversive Consequences. *J. Neurosci* 2000, 20, 3442–8].

Modification of the His in the six position by Pro in the MTII peptide template, resulted in the identification of modifications that might lead to increased MC4R selectivity versus the MC3R [Bednarek, M. A. et al, Analogs of MTII, Lactam Derivatives of α-Melanotropin, Modified at the N-terminus, and their Selectivity at Human Melanocortin Receptors 3, 4, and 5. *Biochem. Biophys. Res. Commun.* 1999, 261, 209–213.]

More recently, modification of the MTII lactam cyclization ring size of peptides containing the His-DPhe-Arg-Trp sequence resulted in identification of 50-fold and 90-fold [Bednarek, M. A. et al, Potent and Selective Peptide Agonists of α-Melanotropin Action at Human Melanocortin Receptor 4: Their Synthesis and Biological Evaluation in Vitro. *Biochem. Biophys. Res. Commun.* 2001, 286, 641–645] MC4 versus MC3 receptor selectivity. Incorporation of the unusual amino acid, Atc in its racemic form at the six position in the peptide c[Asp-(racemic)Atc-DPhe-Arg-TrpLys]-$NH_2$, resulted in a peptide possessing 65 nM agonist activity at the human MC4R while possessing only slight agonist activity at the hMC3R (Danho, id.). This latter report is the first public disclosure of a compound possessing what appears to be "complete" MC4R agonist selectivity versus the MC3R. The JRH42O-12 tetrapeptide (Ac-Anc-DPhe-Arg-Trp-$NH_2$) reported herein possesses >4700-fold MC4R versus MC3R agonist selectivity and an MMC4R $EC_{50}$ value of 21 nM (Table 2) which is 3-fold more potent than the larger c[Asp-(racemic)Atc-DPhe-Arg-Trp-Lys]-$NH_2$ peptide described above. Thus, the invention has identified a tetrapeptide possessing nM potency at the mMC4R (only 4-fold less potent than the endogenous α-MSH agonist) with only weak μM antagonist activity at the other central melanocortin receptor MC3R.

Both the central MC3 and MC4 receptors are located in the hypothalamus of the brain and are implicated in physiologically participating in energy homeostasis that includes the processes of feeding behavior and metabolism. Selective compounds for either of these central melanocortin receptors are highly valuable in order to clearly differentiate the roles of the MC3R versus MC4R in energy homeostasis. It is demonstrated herein that the melanocortin tetrapeptide agonist Ac-Anc-DPhe-Arg-Trp-$NH_2$ possesses MC4 versus MC3 receptor selectivity (21 nM MC4R potency while only weak μM antagonism at the MC3R). This highly potent MC4R selective agonist is highly valuable as a tool to help understand the physiological role(s) that the MC4R contributes to feeding behavior, energy homeostasis, and other physiological functions linked to the central melanocortin receptors.

An additional embodiment of the invention comprises the tetrapeptide Ac-His-(pI)DPhe-Arg-Trp-$NH_2$ that is a full nM agonist at the mMC1 and mMC5 receptors, a potent mMC3R antagonist ($pA_2$=7.25, Ki=56 nM) and partial agonist, but unexpectantly, is a potent agonist at the mMC4R ($EC_{50}$=25 nM). This ligand possesses novel melanocortin receptor pharmacology, compared to previously reported peptides, and is potentially useful for in vivo studies to differentiate MC3R versus MC4R physiological roles in animal models, such as primates, where "knock-out" animals are not viable options. The (pI)DPhe containing tetrapeptide maintained equipotency at the mMC1R, mMC4R, and mMC5R (within the inherent 3-fold experimental error) with DPhe, but was a potent antagonist, $pA_2$=7.25 (Ki=56 nM) at the mMC3R. Surprisingly, the tetrapeptide containing the (pI)DPhe amino acid resulted in a potent mMC4R agonist ($EC_{50}$=25 nM) that is only 5-fold less potent than α-MSH, instead of an antagonist pharmacology like at the mMC3R.

A significant embodiment of the invention, therefore is the tetrapeptide, Ac-His-(pI)DPhe-Arg-Trp-$NH_2$, that possesses novel melanocortin receptor pharmacology in that it is a MC3R antagonist ($pA_2$=7.25, Ki=56 nM) with partial agonist activity, but unexpectantly, possess 25 nM mMC4R agonist activity. This molecule is, therefore, also a physiologically useful compound for differentiating the MC3R versus MC4R in vivo activities in wild-type, non-genetically modified rodents and even primates where knocking out a particular receptor to study physiology is more difficult and costly.

Reference is made to U.S. Pat. Nos. 5,726,156; 5,420,109; 5,741,774; 5,760,001; 5,786,332; 5,888,969; 6,245,738 and 6,284,735; all of which relate to peptides exhibiting cytokine related physiological actions. U.S. Pat. No. 5,726,156 does mention tetrapeptides which are structurally similar to those contained herein and also mentions obesity. All of these patents relate to certain (pI)DPhe amino acids in the context of larger (containing 7 amino acids) cyclic peptides. The tetrapeptides of the present invention have unexpected pharmacology that is different than the incorporation of the (pI)DPhe into larger peptide templates. The peptides of the invention, while they possess partial agonist and antagonist pharmacology at the MC3R (like the above mentioned peptides), contrary to the above larger peptides, they are potent agonists at the MC4R. Thus, this smaller tetrapeptide possesses unexpected pharmacology at the brain melanocortin receptors involved in feeding behavior and obesity, with an agonist for the MC4R a potential therapeutic drug for eating less food, and hence decreasing obesity and obesity related diseases such as hypertension, type II diabetes, stroke, cancer, and morbidity.

The invention claimed is:

1. A peptide derivative having the formula:

$X^1$-Z-Q-arg-trp-$NH_2$, wherein:
$X^1$ is an acyl group,
Z is amino-2-naphthyl-carboxylic acid or histidine,
Q is p-iodo-(D)phenylalanine,
or a pharmacologically acceptable salt, or complex thereof, said peptide derivative having melanocortin-4 receptor agonist activity.

2. The peptide derivative according to claim 1 wherein $X^1$ is acetyl.

3. A peptide derivative having the formula:

$X^1$-Z-Q-arg-trp-$NH_2$, wherein:
$X^1$ is an acyl group,
Z is amino-2-naphthyl-carboxylic acid,
Q is (D)phenylalanine or p-iodo-(D)phenylalanine,
or a pharmacologically acceptable salt or complex thereof, said peptide derivative having melanocortin-4 receptor agonist activity.

4. The peptide derivative according to claim 1 wherein Z is histidine.

5. The peptide derivative according to claim 3 wherein Q is (D)phenylalanine.

6. The peptide derivative according to claim 3 wherein Q is p-iodo-(D)phenylalanine.

7. The peptide derivative according to claim 3 having the formula: acetyl-[amino-2-naphthylcarboxylic acid]-(D)phenylalanine-arginine-tryptophan-$NH_2$, or a pharmacologically acceptable salt or complex.

8. The peptide derivative according to claim 1 having the formula: acetyl-histidine-p-iodo-(D)phenylalanine-arginine-tryptophan-$NH_2$, or a pharmacologically acceptable salt or complex.

9. A composition for the treatment of obesity and the control of appetite in a mammal comprising an effective amount of a peptide derivative of claim 1 in combination with a carrier.

10. A method for the treatment of obesity and control of appetite comprising administering to a mammal in need thereof an effective amount of a peptide derivative according to claim 1.

11. A composition for the treatment of obesity and the control of appetite in a mammal comprising an effective amount of a peptide derivative of claim 3 in combination with a carrier.

12. A method for the treatment of obesity and control of appetite comprising administering to a mammal in need thereof an effective amount of a peptide derivative according to claim 3.

* * * * *

UNITED STATES PATENT AND TRADEMARK OFFICE
CERTIFICATE OF CORRECTION

PATENT NO. : 7,034,004 B2
APPLICATION NO. : 10/139624
DATED : April 25, 2006
INVENTOR(S) : Carrie Haskell-Luevano and Jerry Ryan Holder It is certified that error appears in the above-identified patent and that said Letters Patent is hereby corrected as shown below:

<u>Title Page, item 57 Col. 2, Line 44</u>
Abstract, Line 4, "$X^1$-Z-Q-arg-trp-$NH_{12}$" should read --$X^1$-Z-Q-arg-trp-$NH_2$--.

<u>Column 3,</u>
Lines 65, "The present invention pertains to novel peptides for" should read

--BRIEF DESCRIPTION OF THE SEQUENCE LISTING

The present invention pertains to novel peptides for--.

<u>Column 6,</u>
Line 39, "*Proccedings of*" should read --*Proceedings of*--.

<u>Column 10,</u>
Lines 33-51, Table 2 should read

--

TABLE 2 Functional activity of the tetrapeptide agonists at the mouse melanocortin receptors.

| Peptide | Structure | mMC1R EC50(nM) | mMC3R EC50(nM) | mMC4R EC50(nM) | mMC5R EC50(nM) |
|---|---|---|---|---|---|
| α-MSH (SEQ ID NO:2) | Ac-Ser-Tyr-Ser-Met-Glu-His-Phe-Arg-Trp-Gly-Lys-Pro-Val-NH₂ | 0.55±0.09 | 0.79±0.14 | 5.37±0.62 | 0.44±0.09 |
| NDP-MSH | Ac-Ser-Tyr-Ser-Nle-Glu-His-DPhe-Arg-Trp-Gly-Lys-Pro-Val-NH₂ | 0.038±0.012 | 0.098±0.013 | 0.21±0.03 | 0.071±0.012 |
| MTII | Ac-Nle-c[Asp-His-DPhe-Arg-Trp-Lys]-NH₂ | 0.020±0.003 | 0.016±0.03 | 0.087±0.008 | 0.16±0.03 |
| JRH279-31 | Ac-His-DPhe-Arg-Trp-NH₂ | 20.1±0.57 | 156±9.2 | 17.2±2.78 | 3.96±0.94 |
| JRH420-12 | Ac-Anc-DPhe-Arg-Trp-NH₂ | 7,900±4,200 | Slight agonist pA₂=5.60 | 21.1±5.96 | 45.6±6.90 |
| JRH322-18 | Ac-His-(pI)DPhe-Arg-Trp-NH₂ | 50.4±13.4 | Slight agonist pA₂=7.25 | 25.0±9.78 | 1.60±0.35 |

--

Signed and Sealed this

Second Day of January, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 4

```
<212> TYPE: PRT
<213> ORGANISM: Artificial Sequence
<220> FEATURE:
<223> OTHER INFORMATION: Peptide fragment

<400> SEQUENCE: 1

His Phe Arg Trp
1

<210> SEQ ID NO 2
<211> LENGTH: 13
<212> TYPE: PRT
<213> ORGANISM: Artificial Sequence
<220> FEATURE:
<223> OTHER INFORMATION: Endogenous agonist hormone

<400> SEQUENCE: 2

Ser Tyr Ser Met Glu His Phe Arg Trp Gly Lys Pro Val
1               5                   10
```